US008535607B2

(12) United States Patent
Wakamiya et al.

(10) Patent No.: US 8,535,607 B2
(45) Date of Patent: Sep. 17, 2013

(54) SAMPLE ANALYZER

(75) Inventors: Yuji Wakamiya, Kobe (JP); Tomohiro Okuzaki, Himeji (JP); Hisato Takehara, Kobe (JP)

(73) Assignee: Sysmex Corporation, Kobe (JP)

( * ) Notice: Subject to any disclaimer, the term of this patent is extended or adjusted under 35 U.S.C. 154(b) by 1217 days.

(21) Appl. No.: 12/079,797

(22) Filed: Mar. 28, 2008

(65) Prior Publication Data

US 2008/0240984 A1 Oct. 2, 2008

(30) Foreign Application Priority Data

Mar. 29, 2007 (JP) ................................ 2007-086872

(51) Int. Cl.
*G01N 15/06* (2006.01)
*G01N 33/00* (2006.01)
*G01N 33/48* (2006.01)

(52) U.S. Cl.
USPC ................ 422/64; 422/50; 422/63; 422/65; 422/66; 422/67; 422/81; 422/82.01; 422/82.05; 436/43; 436/47; 436/174; 436/180

(58) Field of Classification Search
USPC ............ 422/50, 63, 64, 65, 66, 67, 81, 82.01, 422/82.05, 68.1; 436/43, 47, 63, 66, 54, 436/67, 68, 69, 70, 71, 174, 180
See application file for complete search history.

(56) References Cited

U.S. PATENT DOCUMENTS

| 2005/0047964 A1* | 3/2005 | Nishida et al. ................. 422/64 |
| 2009/0082984 A1* | 3/2009 | Wakamiya et al. ............. 702/85 |
| 2009/0215184 A1* | 8/2009 | Wakamiya et al. ............. 436/50 |
| 2010/0238043 A1* | 9/2010 | Wakamiya et al. ........ 340/691.6 |

FOREIGN PATENT DOCUMENTS

JP 2002-350451 12/2002

* cited by examiner

*Primary Examiner* — Brian J Sines
(74) *Attorney, Agent, or Firm* — Brinks Hofer Gilson & Lione

(57) ABSTRACT

The present invention is to present a sample analyzer which is capable of prevent consumable part which does not adapt to the sample analyzer from being used and maintain measurement precision. The sample analyzer 10 includes barcode reader 60 for obtaining serial number for identifying pipette tip 80 from barcode 83; containing section 21*a* for containing pipette tips 80 used by a predetermined mechanism section; CPU 34*a* for obtaining a number of the pipette tips 80 which have been used by the mechanism section; CPU 51*a* for obtaining a number of the usable pipette tips 80; warning screens 76, 77, 79 for giving a predetermined warning to a user, when the number obtained by CPU 34*a* is in a predetermined relationship with the number obtained by CPU 51*a*.

9 Claims, 12 Drawing Sheets

SAMPLE ANALYZER

RELATED APPLICATIONS

This application claims priority under 35 U.S.C. §119 to Japanese Patent Application No. 2007-086872 filed Mar. 29, 2007, the entire contents of which are hereby incorporated by reference.

FIELD OF THE INVENTION

The present invention relates to a sample analyzer, in particular, to a sample analyzer for analyzing a sample using a consumable part.

BACKGROUND

Recently, in the field of clinical examinations, there are a lot of sample analyzers that use pipette tips and cuvettes as disposable consumable parts to reduce contamination. There is a tendency to reduce the sample amount to be collected to alleviate the load on the patient, and finer amount of the sample to be measured and enhancement in measurement precision thereof are being desired. Therefore, the performance of the pipette tip and the cuvette influences the measurement precision of the sample analyzer. For example, in the pipette tip, the inner diameter is very small in order to ensure fine fixed quantity and precision, and the shape of the product becomes more complex. And the cuvette is manufactured by a special material in order to ensure transmissive performance of the light of a certain wavelength and capacity, and the shape of the product becomes more complex. Thus, the measurement precision of the sample analyzer can be ensured by using the pipette tip and the cuvette which predetermined performance is ensured. On the other hand, if the pipette tip and the cuvette that do not adapt to the sample analyzer are used, the measurement precision cannot be maintained, and the analyzing precision by the sample analyzer lowers.

Japanese Laid-Open Patent Publication No. 2002-350451 discloses an automatic analyzer (sample analyzer) capable of automatically managing consumable goods such as reagent and cleaning agent. The sample analyzer disclosed in Japanese Laid-Open Patent Publication No. 2002-350451 determines whether or not the precision of the clinical examination can be guaranteed, based on the consumable good information such as reagent and cleaning agent related to clinical examination and the result of the clinical examination.

However, a method of maintaining the measurement precision of the sample analyzer is not taken into consideration when the consumable part (pipette tip and cuvette) that does not adapt to the sample analyzer is used in Japanese Laid-Open Patent Publication No. 2002-350451. Thus, the measurement precision might lower when the consumable part that does not adapt to the sample analyzer used.

BRIEF SUMMARY

A first aspect of the present invention is a sample analyzer for analyzing a sample using a consumable part, comprising: an identification information obtainer for obtaining group identification information for identifying a group of a plurality of consumable parts; a consumable part holder for holding the consumable parts used by a predetermined mechanism section; first consumable part number obtaining means for obtaining a number of the consumable parts which have been used by the mechanism section; second consumable part number obtaining means for obtaining a number of the consumable parts included in the group, based on the group identification information obtained by the identification information obtainer; and a warning section for giving a predetermined warning to a user, when the number obtained by the first consumable part number obtaining means is in a predetermined relationship with the number obtained by the second consumable part number obtaining means.

A second aspect of the present invention is a sample analyzer for analyzing a sample using a consumable part, comprising: an identification information obtainer for obtaining group identification information for identifying a group of a plurality of consumable parts; a consumable part holder for holding the consumable parts used by a predetermined mechanism section; number of times obtaining means for obtaining the number of times the group identification information is obtained by the identification information obtainer; and a warning section for giving a predetermined warning to a user when the number of times obtained by the number of times obtaining means exceeds a predetermined number.

A third aspect of the present invention is a sample analyzer for analyzing a sample using a consumable part, comprising: an identification information obtainer for obtaining group identification information for identifying a group of a plurality of consumable parts; determining means for determining whether the consumable parts are adapted for the sample analyzer based on the group identification information obtained by the identification information obtainer; and a warning section for giving a predetermined warning to a user when the determining means determines that the consumable parts are not adapted for the sample analyzer.

A fourth aspect of the present invention is a sample analyzer for analyzing a sample using a consumable part, comprising: a container for containing a plurality of consumable parts; a mechanism section which uses the consumable parts contained in the container; first consumable part number obtaining means for obtaining a number of the consumable parts contained in the container; second consumable part number obtaining means for obtaining a number of the consumable parts which have been used by the mechanism section; and a warning section for giving a predetermined warning to a user when the number obtained by the second consumable part obtaining means exceeds the number obtained by the first consumable part number obtaining means.

DETAILED DESCRIPTION OF THE PREFERRED EMBODIMENTS

The embodiments embodying the present invention will be described based on the drawings.

An immunoanalyzer 10 according to one embodiment of the present invention is an apparatus for carrying out examinations on various items such as hepatitis B, hepatitis C, tumor marker, and thyroid hormone using specimens such as blood. In the immunoanalyzer 10, magnetic particles (R2 reagent) are bonded to a trapped antibody (R1 reagent) bonded to an antigen contained in a specimen such as blood, which is the measuring object, and thereafter, the bound antigen, trapped antibody, and magnetic particles are attracted to a magnet (not shown) of a BF (Bound Free) separator 14 (see FIGS. 1 and 2) to remove the R1 reagent containing non-reactive (free) trapped body. A labeled antibody (R3 reagent) is bonded to the antigen bound with magnetic particles, and thereafter, the bound magnetic particles, antigen, and labeled antibody are attracted to a magnet of a BF separator 32 to remove a R3 reagent containing non-reactive (free) labeled antibody. Furthermore, a light emitting substrate (R5 reagent) that emits light in the reaction process with the labeled antibody is added, and a light emitting amount generated through the reaction of the labeled antibody and the light emitting substrate is measured. After such processes, the antigen or the antibody contained in the specimen that bonds with the labeled antibody is quantitatively measured.

Figure 1:
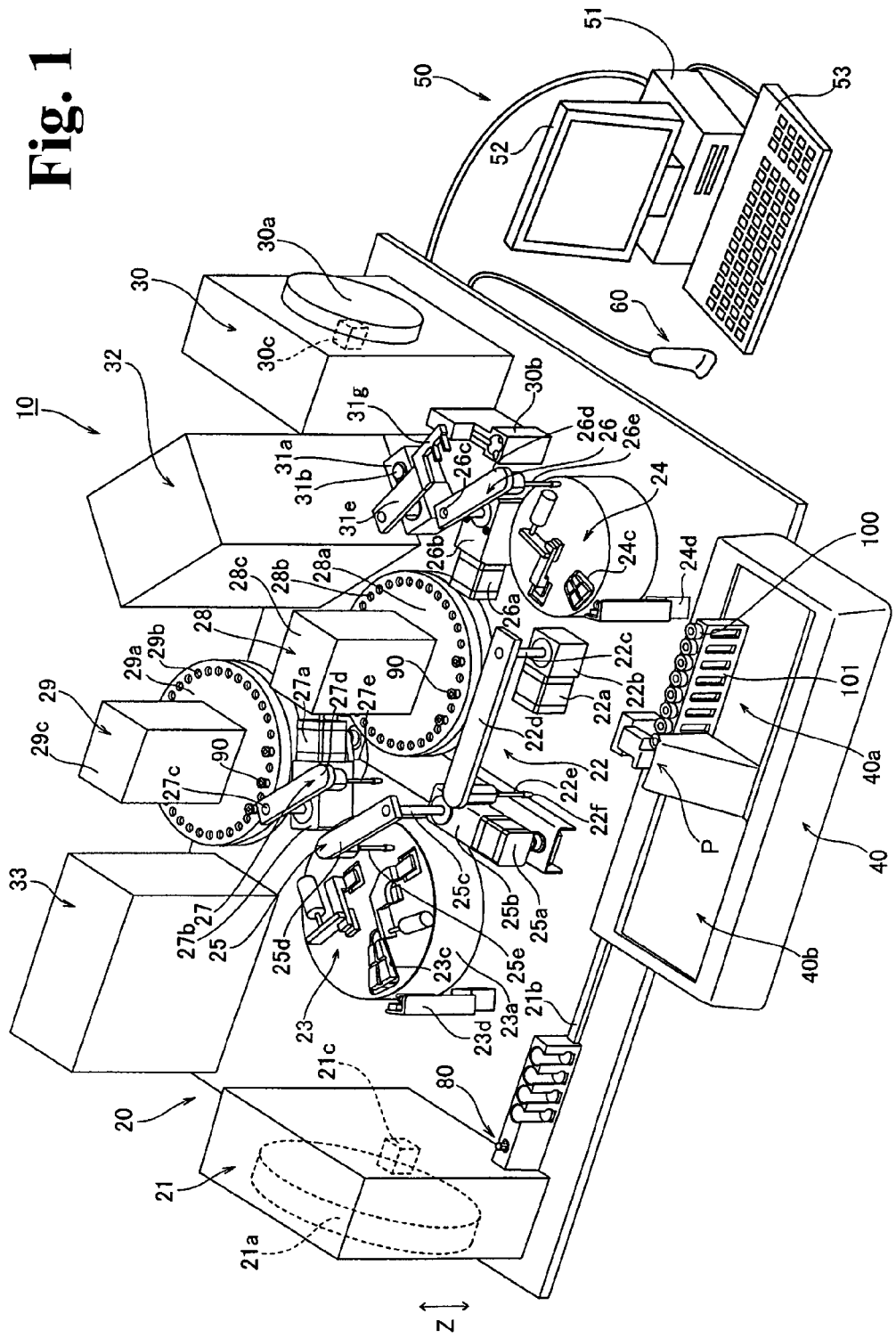
FIG. 1 is a perspective view showing an overall configuration of an immunoanalyzer according to one embodiment of the present invention.
Figure 2:
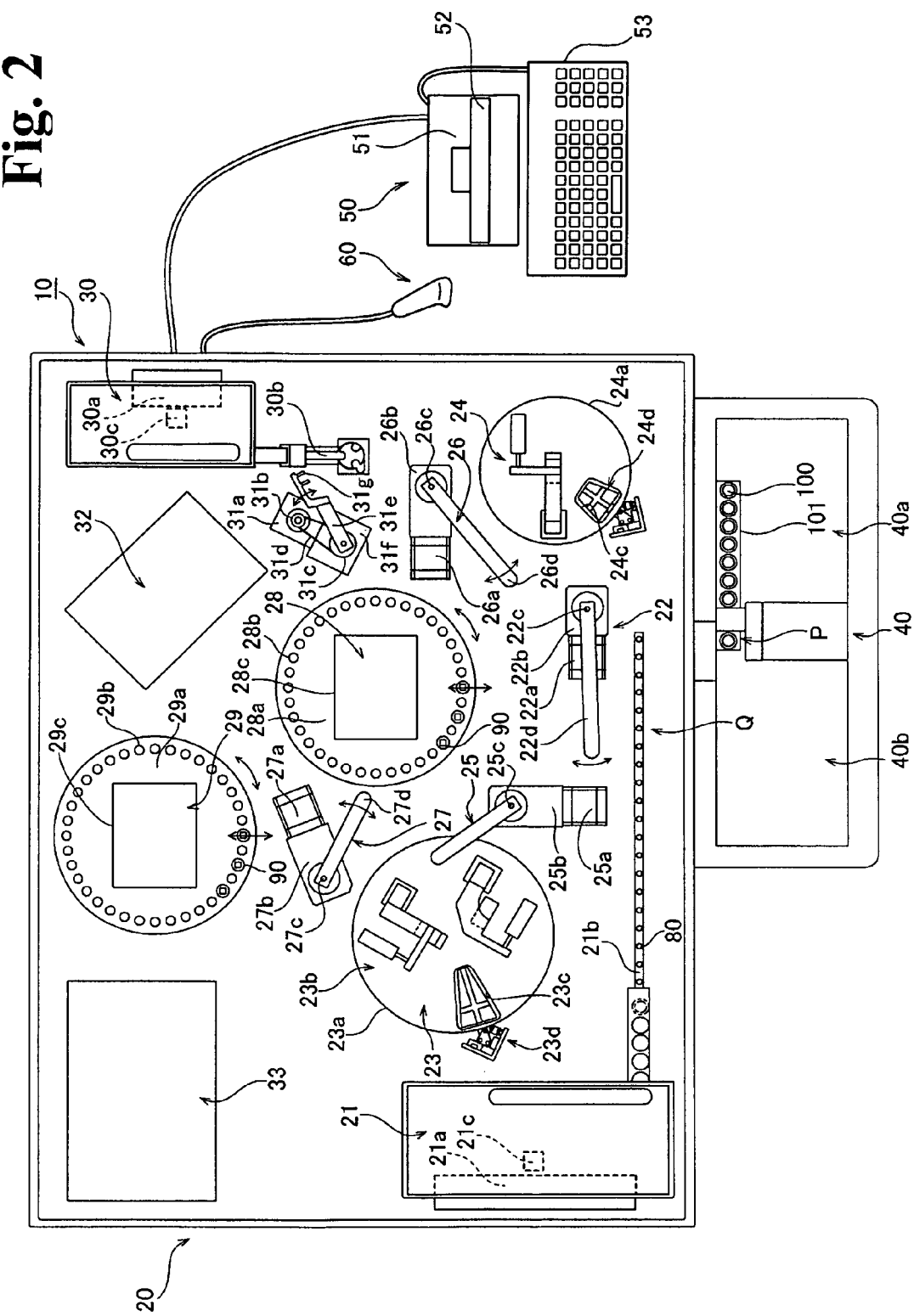
FIG. 2 is a plan view of the immunoanalyzer shown in FIG. 1.
Figure 5:
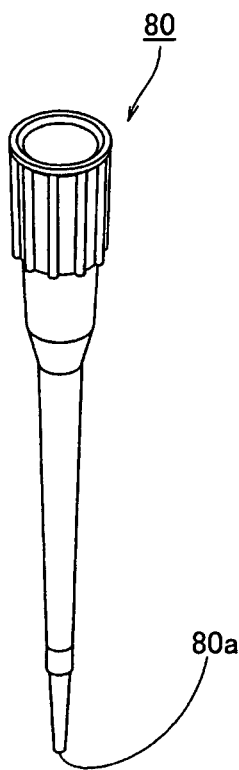
FIG. 5 is a view showing a pipette tip used in the immunoanalyzer according to one embodiment shown in FIG. 1.
Figure 6:
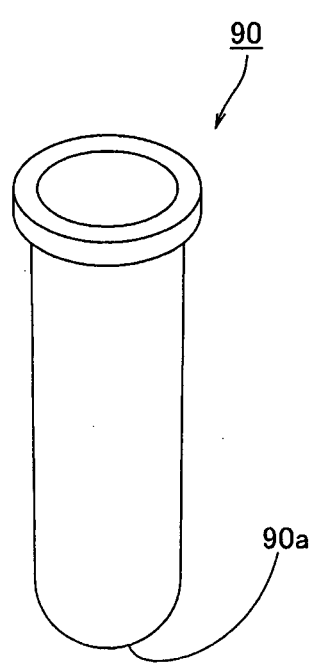
FIG. 6 is a view showing a cuvette used in the immunoanalyzer according to one embodiment shown in FIG. 1.

As shown in FIGS. 1 and 2, the immunoanalyzer 10 includes a measurement mechanism section 20, a specimen conveyance section (sampler) 40 arranged on the front surface side of the measurement mechanism section 20, and a control device 50 including PC (personal computer) electrically connected to the measurement mechanism section 20. The immunoanalyzer 10 is configured to perform the analyzing operation of the sample by using a pipette tip 80 (see FIG. 5) made of resin and a cuvette 90 (see FIG. 6) serving as disposable consumable parts.

Figure 3:
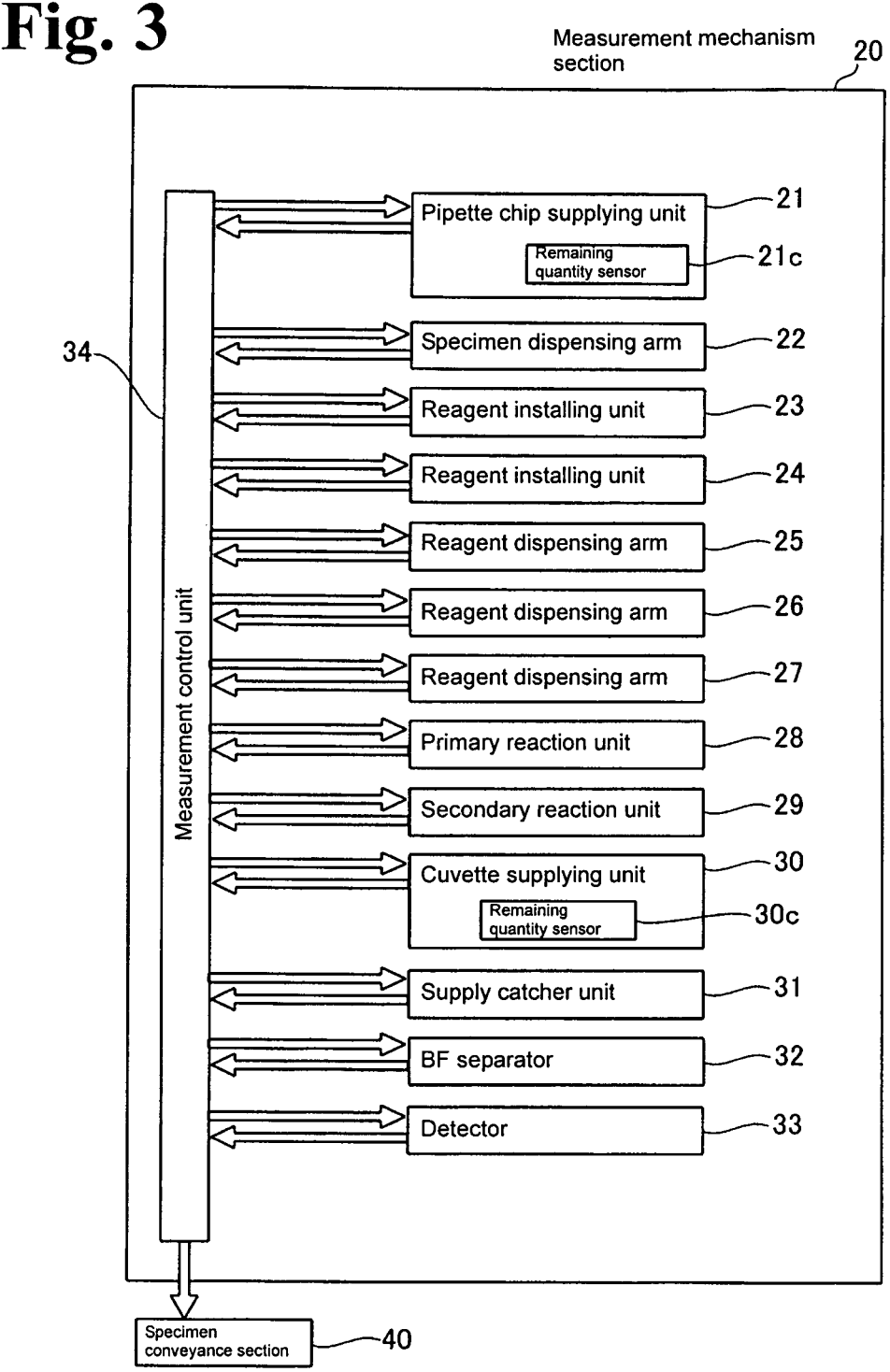
FIG. 3 is a block diagram including a control unit of a measurement mechanism section of the immunoanalyzer according to one embodiment of the present invention.

The measurement mechanism section 20 is configured by a pipette tip supplying unit 21, specimen dispensing arm 22, reagent installing units 23 and 24, reagent dispensing arms 25, 26, and 27, a primary reaction unit 28 and a secondary reaction unit 29, a cuvette supplying unit 30, a supply catcher unit 31, a BF separator 32, and a detector 33. As shown in FIG. 3, each mechanism section (pipette tip supplying unit 21, specimen dispensing arm 22, reagent installing unit 23, reagent installing unit 24, and reagent dispensing arm 25 the like) in the measurement mechanism section 20 are controlled by a measurement control unit 34 (see FIG. 3) arranged in the measurement mechanism section 20. Specifically, the measurement control unit 34 receives signals of various sensors (origin detection sensor etc. (not shown)) arranged in each mechanism section, and controls the drive of various drive sources (stepping motor etc. (not shown) arranged in each mechanism section. The specimen conveyance section 40 is also controlled by the measurement control unit 34.

The pipette tip supplying unit 21 (see FIGS. 1 and 2) has a function of conveying a plurality of pipette tips 80 (see FIG. 5) supplemented in a containing section 21a by the user one at a time up to an attachment position Q (see FIG. 2) of the specimen dispensing arm 22 with a distal end 90a of the pipette tip 80 directed downward by the conveyance section 21b. A remaining quantity sensor (transmissive sensor) 21c for detecting the presence (remaining quantity) or absence of the pipette tip 80 contained in the containing section 21a is arranged in the pipette tip supplying unit 21.

Figure 7:
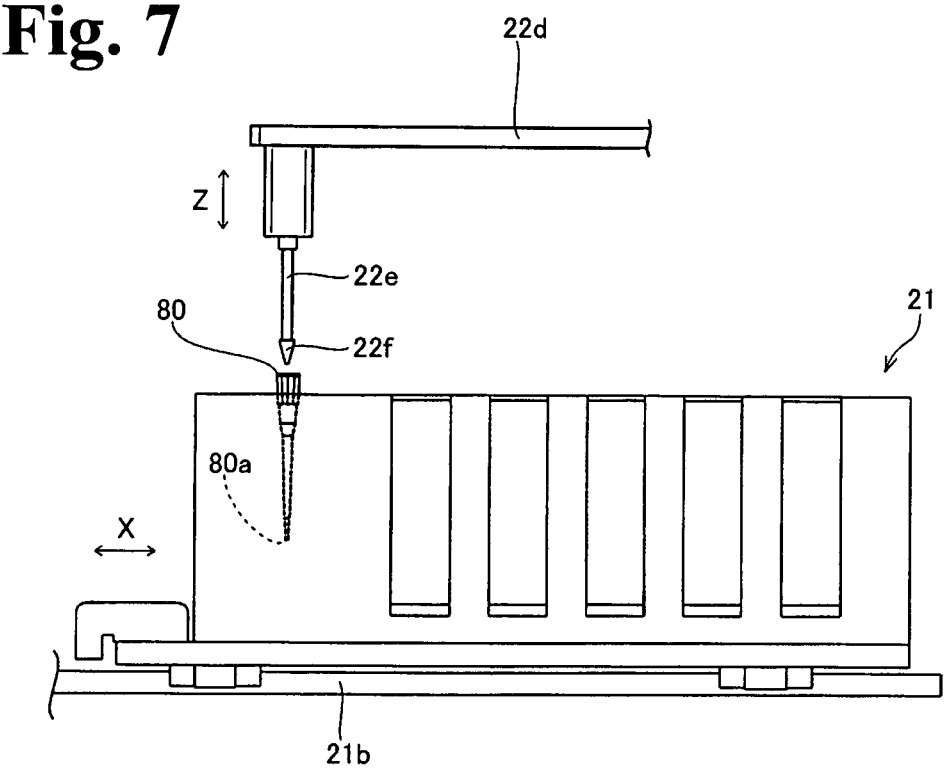
FIG. 7 is a side view showing a specimen dispensing arm of the immunoanalyzer according to one embodiment shown in FIG. 1.

The specimen dispensing arm 22 (see FIGS. 1 and 2) has a function of dispensing the specimen in the test tube 100 conveyed to an aspirating position P by the specimen conveyance section 40 into a cuvette 90 held by a holder 28b of a rotatable table 28a of the primary reaction unit 28 to be described later. As shown in FIGS. 1 and 2, the specimen dispensing arm 22 includes a motor 22a, a drive transmission part 22b connected to the motor 22a, and an arm 22d attached to the drive transmission part 22b by way of a shaft 22c. The drive transmission part 22b is configured to rotate the arm 22d with the shaft 22c as the center by the driving force from the motor 22a, and move the arm in the up and down direction (Z direction). A nozzle 22e for aspirating and discharging specimen is attached to the distal end of the arm 25d. As shown in FIG. 7, the pipette tip 80 conveyed to the attachment position Q by the conveyance section 21b of the pipette tip supplying unit 21 is inserted with a distal end 22f of the nozzle 22e of the specimen dispensing arm 22 to attach the pipette tip 80. In the present embodiment, the measurement control unit 34 (see FIG. 3) detects the rotating operation of the arm 22d to recognize the number of pipette tips 80 used in the analyzing operation.

The reagent installing unit 23 (see FIGS. 1 and 2) is arranged to install a reagent-containing assembly for holding a reagent container in which an R1 reagent containing trapped antibody is contained and a reagent container in which a R3 reagent containing labeled antibody is contained. As shown in FIG. 1, the reagent installing unit 23 includes a reagent holder 23a for holding the reagent-containing assembly, a lid 23b attached to the reagent holder 23a, and a raising and lowering unit 23d for replacing the reagent-containing assembly in the reagent holder 23a through a hole 23c formed in the lid 23b.

The reagent installing unit 24 (see FIGS. 1 and 2) is arranged to install a reagent-containing assembly (not shown) for holding a reagent container in which an R2 reagent containing magnetic particles is contained. As shown in FIG. 1, the reagent installing unit 24 includes a reagent holder 24a for holding the reagent-containing assembly, a lid 24b attached to the reagent holder 24a, and a raising and lowering unit 24d for replacing the reagent-containing assembly in the reagent holder 24a through a hole 24c formed in the lid 24b.

The reagent dispensing arm 25 (see FIGS. 1 and 2) has a function of aspirating the R1 reagent in the reagent-containing assembly installed in the reagent installing unit 23 and dispensing the aspirated R1 reagent into the cuvette 90 dispensed with the specimen of the primary reaction unit 28. The reagent dispensing arm 25 includes a motor 25a, a drive transmission part 25b connected to the motor 25a, and an arm 25d attached to the drive transmission part 25b by way of a shaft 25c. The drive transmission part 25b is configured to rotate the arm 25d with the shaft 25c as the center by the driving force from the motor 25a, and move the arm in the up and down direction. A pipette 25e (see FIG. 1) for aspirating and discharging the R1 reagent in the reagent-containing assembly is attached to the distal end of the arm 25d. That is, the pipette 25e is configured to aspirate the R1 reagent in the reagent-containing assembly installed in the reagent installing unit 23, and thereafter, dispense the aspirated R1 reagent into the cuvette 90 dispensed with the specimen of the primary reaction unit 28.

The reagent dispensing arm 26 (see FIGS. 1 and 2) has a function of dispensing the R2 reagent in the reagent-containing assembly installed in the reagent installing unit 24 into the cuvette 90 dispensed with the specimen and the R1 reagent of the primary reaction unit 28. The reagent dispensing arm 26 includes a motor 26a, a drive transmission part 26b connected to the motor 26a, and an arm 26d attached to the drive transmission part 26b by way of a shaft 26c. The drive transmission part 26b is configured to rotate the arm 26d with the shaft 26c as the center by the driving force from the motor 26a, and move the arm in the up and down direction. A pipette 26e (see FIG. 1) for aspirating and discharging the R2 reagent in the reagent-containing assembly installed in the reagent installing unit 24 is attached to the distal end of the arm 26d. Thus, the pipette 26e is configured to aspirate the R2 reagent in the reagent-containing assembly installed in the reagent installing unit 24, and thereafter, dispense the aspirated R2 reagent into the cuvette 90 dispensed with the specimen and the R1 reagent of the primary reaction unit 28.

The reagent dispensing arm 27 (see FIGS. 1 and 2) has a function of aspirating the R3 reagent in the reagent-containing assembly installed in the reagent installing unit 23, and dispensing the aspirated R3 reagent into the cuvette 90 dispensed with the specimen, the R1 reagent, and the R2 reagent of the secondary reaction unit 29. The reagent dispensing arm 27 includes a motor 27a, a drive transmission part 27b connected to the motor 27a, and an arm 27d attached to the drive transmission part 27b by way of a shaft 27c. The drive transmission part 27b is configured to rotate the arm 10d with the shaft 27c as the center by the driving force from the motor 27a, and move the arm in the up and down direction. A pipette 27e (see FIG. 1) for aspirating and discharging the R3 reagent in the reagent-containing assembly is attached to the distal end of the arm 27d. That is, the pipette 27e is configured to aspirate the R3 reagent in the reagent-containing assembly installed in the reagent installing unit 23, and thereafter, dispense the aspirated R3 reagent into the cuvette 90 dispensed with the specimen, the R1 reagent, and the R2 reagent of the secondary reaction unit 29.

As shown in FIGS. 1 and 2, the primary reaction unit 28 is arranged to rotatably transport the cuvette 90 held by the holder 28b of the rotatable table 28a by a predetermined angle for every predetermined period (18 seconds in the present embodiment), and to stir the specimen, the R1 reagent, the and the R2 reagent in the cuvette 90. That is, the primary reaction unit 28 is arranged to react the R2 reagent containing magnetic particles and the antigen in the specimen in the cuvette 90. The primary reaction unit 28 is configured by a rotatable table 28a for conveying the cuvette 90 containing the specimen, the R1 reagent, and the R2 reagent in the rotating direction, and a container conveying part 28c for stirring the specimen, the R1 reagent, and the R2 reagent in the cuvette 90 and conveying the cuvette 90 containing the stirred specimen, R1 reagent and R2 reagent to the BF separator 32 (see FIGS. 1 and 2) to be described later.

The rotatable table 28a is configured so as to rotatably transport the cuvette 90 held in the holder 28b by a predetermined angle every 18 seconds. Thus, various devices (specimen dispensing arm 22, reagent dispensing arms 25 and 26 etc.) of the immunoanalyzer 10 are controlled so as to operate on the cuvette 90 at the predetermined transported position at a timing the cuvette is transported to the predetermined position by the rotatable table 28a.

The container conveying part 28c is rotatably arranged at the central portion of the rotatable table 28a. The container conveying part 28c has a function of gripping the cuvette 90 held in the holder 28b of the rotatable table 28a and stirring the sample in the cuvette 90. Furthermore, the container conveying part 28c has a function of transporting the cuvette 90 containing the sample obtained by stirring and incubating the specimen, the R1 reagent and the R2 reagent to the BF separator 32 (see FIGS. 1 and 2).

The secondary reaction unit 29 (see FIGS. 1 and 2) has a configuration similar to the primary reaction unit 28, and is arranged to rotatably transport the cuvette 90 held by the holder 29b of the rotatable table 29a by a predetermined angle for every predetermined period (18 seconds in the present embodiment), and to stir the specimen, the R1 reagent, the R2 reagent, the R3 reagent, and the R5 reagent in the cuvette 90. That is, the secondary reaction unit 29 is arranged to react the R3 reagent containing labeled antibody and the antigen in the specimen in the cuvette 90, and to react the R5 reagent containing light emitting substrates and the labeled antibody of the R3 reagent. The R5 reagent is dispensed into the cuvette 90 containing the specimen, the R1 reagent, the R2 reagent, and the R3 reagent of the secondary reaction unit 29 by a R5 reagent dispensing arm (not shown) arranged near the secondary reaction unit 29. The secondary reaction unit 29 is configured by a rotatable table 29a for conveying the cuvette 90 containing the specimen, the R1 reagent, the R2 reagent, the R3 reagent, and the R5 reagent in the rotating direction, and a container conveying part 29c for stirring the specimen, the R1 reagent, the R2 reagent, R3 reagent, and the R5 reagent in the cuvette 90 and conveying the cuvette 90 containing the stirred specimen etc. to the BF separator 32. The container conveying part 29c has a function of again conveying the cuvette 90 processed by the BF separator 32 to the holder 29b of the rotatable table 29a. The detailed structure of the secondary reaction unit 29 is similar to the primary reaction unit 28, and thus the description thereof will be omitted.

The cuvette supplying unit 30 (see FIGS. 1 and 2) is configured to convey a plurality of cuvettes 90 (see FIG. 6) supplemented by the containing section 30a by the user one at a time with the bottom part 80a of the cuvette 90 directed downward by the conveyance section 30b, and to sequentially supply the plurality of cuvettes 90 to the holder 28b of the rotatable table 28a of the primary reaction unit 28 from the conveyance section 30b by the supply catcher unit 31 arranged adjacent to the cuvette supplying unit 30. A remaining quantity sensor (transmissive sensor) 30c for detecting the presence (remaining quantity) or absence of the cuvette 90 contained in the containing section 30a is arranged in the cuvette supplying unit 30.

The supply catcher unit 31 (see FIG. 1) has a function of transporting the cuvette 90 received by the conveyance section 30b of the cuvette supplying unit 30 to the holder 20b of the rotatable table 28a of the primary reaction unit 28. The supply catcher unit 31 includes a motor 31a, a pulley 31b connected to the motor 31a, a pulley 31c arranged with a predetermined interval with the pulley 31b, a drive transmission belt 31d attached to the pulley 31b and the pulley 31c, an arm 31e attached to the pulley 31c by way of a shaft, and a drive part 31f for moving the arm 31e in the up and down direction (Z direction). Furthermore, a chuck part 31g for sandwiching and gripping the cuvette 90 is arranged at the distal end of the arm 31e. In the present embodiment, the number of cuvettes 90 to be used can be recognized by detecting the rotating operation of the arm 31e with the measurement control unit 34 (see FIG. 3).

The BF separator 32 has a function of separating the non-reacting R1 reagent (unnecessary component) and the magnetic particles from the sample in the cuvette 90 conveyed by the container conveying part 28c of the primary reaction unit 28, and a function of separating the non-reacting R3 reagent (unnecessary component) and the magnetic particles from the sample in the cuvette 90 (see FIG. 1) conveyed by the container conveying part 29c of the secondary reaction unit 29.

The detector 33 (see FIGS. 1 and 2) is arranged to measure the amount of antigen contained in a specimen by obtaining the light generated in the reaction process of the labeled antibody bound to the antigen of the specimen performed with a predetermined process and the light emitting substrate with a photo multiplier tube.

Figure 4:
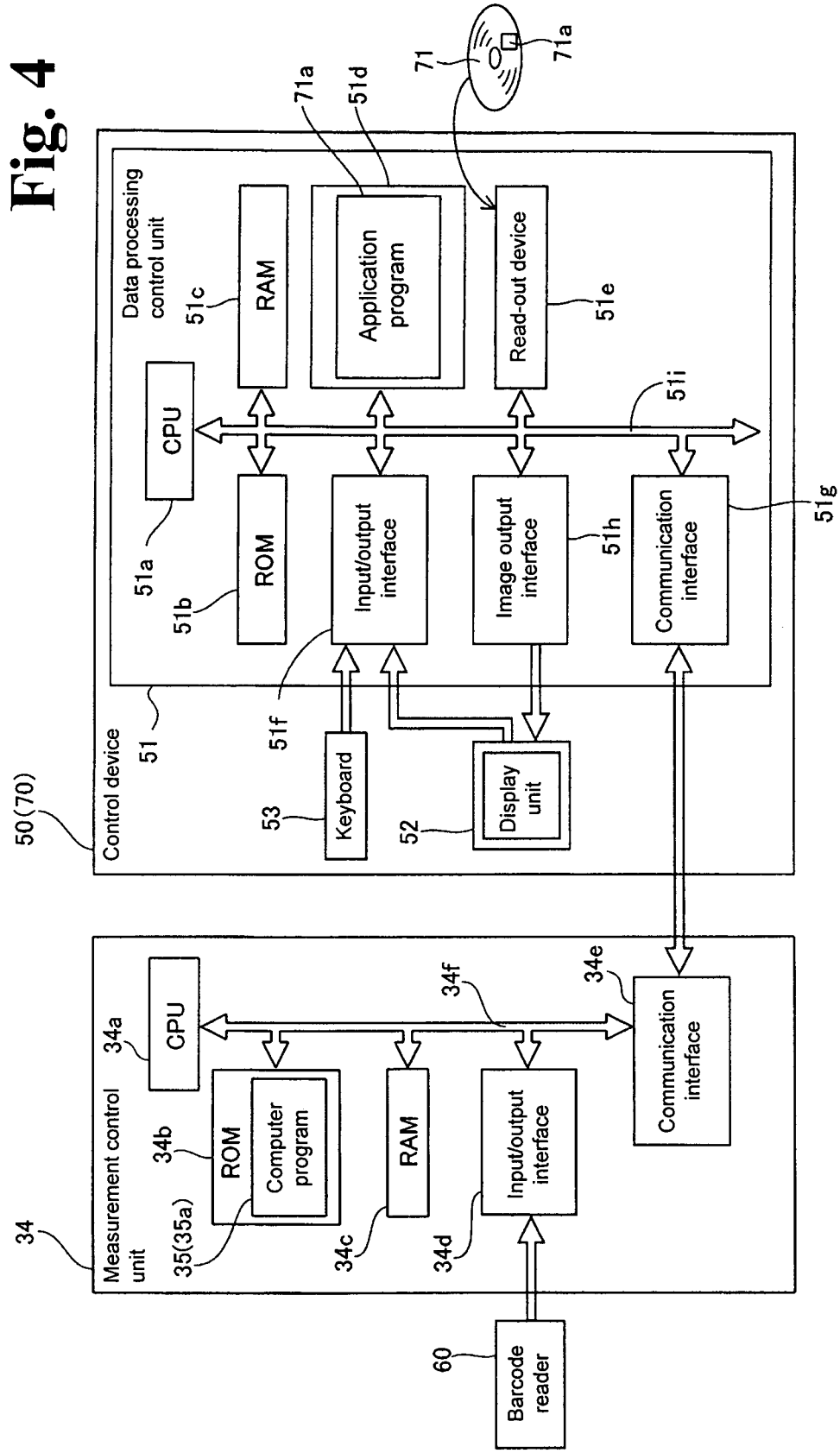
FIG. 4 is a block diagram showing an overall configuration of the measurement mechanism section and the control device of the immunoanalyzer according to one embodiment of the present invention.

As shown in FIG. 4, the measurement control unit 34 is mainly configured by a CPU 34a, a ROM 34b, a RAM 34c, an input/output interface 34d, and a communication interface 34e, which are connected to each other by a bus 34f so that control signal and calculation data etc. in control can be exchanged with each other.

The control unit 34a executes a computer program 35 stored in the ROM 34b and a computer program 35 read by the RAM 34c. The ROM 34b stores computer program 35 executable by the CPU 34a, data used in executing the computer program 35, and the like. The RAM 34c is used to read out the computer program 35 (see FIG. 4) stored in the ROM 34b. In executing the computer program 35, the ROM 34c is used as a work region of the CPU 34a. In the present embodiment, a counter 35a is arranged in the computer program 35 as a variable. The counter 35a is configured to store the number of pipette tip 80 and the cuvette 90 used in the analyzing operation in the computer program 35 executed by the CPU 34a.

The input/output interface 34d is connected to a barcode reader 60 (see FIG. 1), and has a function of transmitting information of a barcode 83 (see FIG. 8) arranged at a side surface of a package (box 81 (see FIG. 8)) containing the consumable part to be described later (pipette tip 80, cuvette 90, and the like) to the measurement control unit 34. The communication interface 34e is connected to the communication interface 51g on the control device 50 side, and has a function of transmitting optical information (data of light emitting amount generated by reaction of the labeled antibody and light emitting substrate) of the specimen to the control device 50, and receiving signals from the data processing control unit 51 of the control device 50. The communication interface 34e has a function of transmitting a command from the CPU 34a for driving each unit of the measurement mechanism section 20 and the specimen conveyance section 40.

As shown in FIGS. 1 and 2, the specimen conveyance section 40 is configured to convey a rack 101 mounted with a plurality of test tubes 100 containing the specimen to a position corresponding to the aspirating position P at where the specimen dispensing arm 22 aspirates the specimen. The specimen conveyance section 40 includes a rack set part 40a for setting the rack 101 in which the test tubes 100 containing non-processed specimen are mounted, and a rack storing part 40b for storing the rack 101 in which the test tubes 100 containing the dispensing processed specimen are mounted. The test tube 100 containing the non-processed specimen is conveyed to a position corresponding to the aspirating position P of the specimen dispensing arm 22, so that the specimen dispensing arm 22 aspirates the specimen such as blood in the test tube 100, and thereafter, the rack 101 mounted with the test tube 100 is stored in the rack storing part 40b.

The control device 50 (FIG. 1) consists of a personal computer (PC), and includes a computer 70 mainly configured by a data processing control unit 51 including CPU, ROM, RAM, a display unit 52 and a keyboard 53. The data processing control unit 51 is mainly configured by a CPU 51a, a ROM 51b, a RAM 51c, a hard disc 51d, a read-out device 51e, an input/output interface 51f, a communication interface 51g and an image output interface 51h. The CPU 51a, the ROM 51b, the RAM 51c, the hard disc 51d, the read-out device 51e, the input/output interface 51f, the communication interface 51g, and the image output interface 51h are connected by a bus 51i, so that control signals and calculation data in control can be exchanged with each other. The display unit 52 is arranged to display the result of analysis etc. obtained by analyzing the data of the digital signal transmitted from the detector 33. In the present embodiment, operation related to supplementing the consumable parts (pipette tip 80, cuvette 90, and the like) can be performed in the control device 50.

The CPU 51a executes computer programs stored in the ROM 51b and the computer programs loaded in the RAM 51c. The CPU 51a executes the immune analysis application program 71a, as described later, so that the computer 70 functions as the control device 50.

The ROM 51b is configured by mask ROM, PROM, EPROM, EEPROM, and the like, and is stored with computer programs to be executed by the CPU 51a, data used for the same, and the like. The RAM 51c is configured by SRAM, DRAM, and the like. The RAM 51c is used to read out the computer programs stored in the ROM 51b and the hard disc 51d. The RAM 51c is used as a work region of the CPU 51a when executing the computer programs.

The hard disc 51d is stored with various computer programs to be executed by the CPU 51a such as operating system and application program, as well as data used in executing the computer program. The immune analysis application program 71a according to the present embodiment is also stored in the hard disc 51d.

The read-out device 51e is configured by flexible disc drive, CD-ROM drive, DVD-ROM drive, and the like, and is able to read out computer programs and data recorded on a portable recording medium 71. The immune analysis application program 71a is stored in the portable recording medium 71, where the computer 70 reads out the application program 71a from the portable recording medium 71, and installs the application program 71a to the hard disc 51d.

The application program 71a is not only provided by the portable recording medium 71, but also provided through communication line (wired or wireless) from external devices communicatably connected with the computer 70 through the communication line. For instance, the application program 71a may be stored in the hard disc of the server computer on the Internet, so that the computer 70 can access the server computer to download the application program 71a and install the application program 71a to the hard disc 51d.

Operating system providing graphical user interface environment such as Windows (registered trademark) manufactured and sold by US Microsoft Co. is installed in the hard disc 51d. In the following description, the application program 71a according to the present embodiment is assumed to operate on the operating system.

The input/output interface 51f is configured by serial interface such as USB, IEEE1394, RS-232C; parallel interface such as SCSI, IDE, IEEE1284; analog interface such as D/A converter, A/D converter, and the like. The keyboard 53 is connected to the input/output interface 51f, so that the user can input data to the computer 70 using the keyboard 53.

The communication interface 51g is, for example, Ethernet (registered trademark) interface. The computer 70 transmits and receives data with the measurement mechanism section 20 using a predetermined communication protocol by means of the communication interface 51g.

The image output interface 401h is connected to the display unit 52 configured by LCD, CRT, or the like, and is configured to output an image signal corresponding to the image data provided from the CPU 51a to the display unit 52. The display unit 52 displays the image (screen) according to the input image signal.

The immune analysis application program 71a installed in the hard disc 51d of the data processing control unit 51 has a main function of measuring the amount of antigen or antibody in the measurement sample using the light emitting amount (data of digital signal) of the measurement sample transmitted from the detector 3 of the measurement mechanism section 20.

Figure 8:
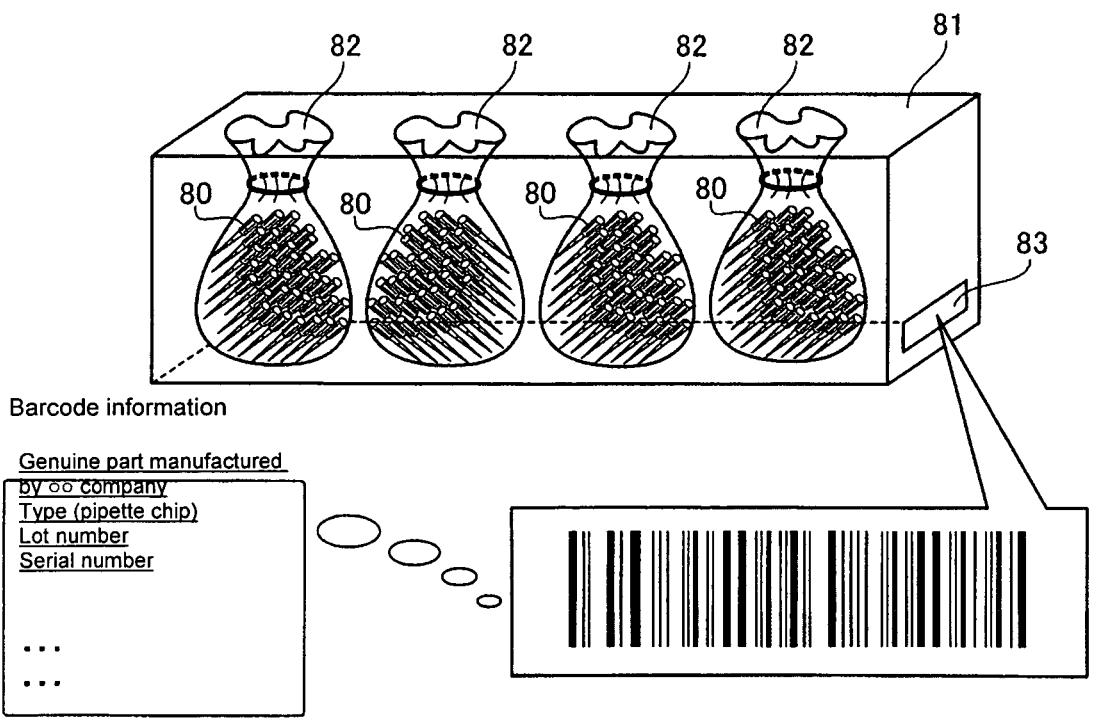
FIG. 8 is a view showing a contained state of a consumable part used in the immunoanalyzer according to one embodiment shown in FIG. 1.

As shown in FIG. 8, the pipette tip 80 is commercially available to the user by containing four in a small bag 82 segmented and bagged into plurals (in units of five hundred in the present embodiment) in the box 81. Therefore, the box 81 contains 2000 pipette tips 80 per box. As shown in FIG. 8, the barcode 83 is attached to the side surface of the box 81. Information such as "manufacturing company information (genuine part of oo Company)", "type (pipette tip)", "lot number" and "serial number" are recorded in the barcode 83 as barcode information, and such information is read by the barcode reader 60. The mode of supplying the commercially available cuvette 90 is similar to the mode of supplying the pipette tip 80, and thus the description thereof will be omitted.

The screen configuration of the application program 71a applied in the immunoanalyzer 10 will now be described with reference to FIGS. 9 to 14.

Figure 9:
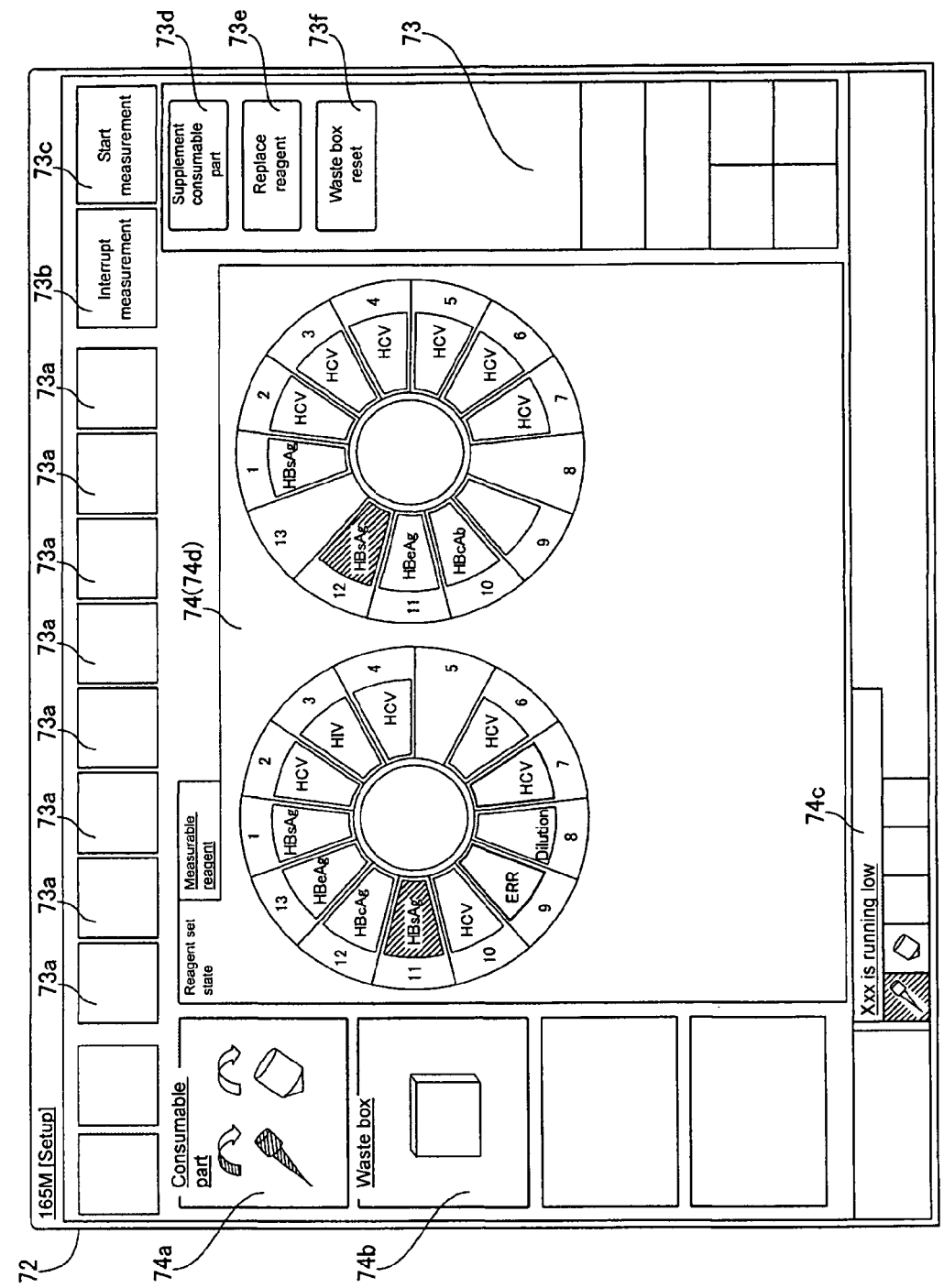
FIG. 9 is a view showing an operation screen displayed in the immunoanalyzer according to one embodiment of the present invention.

When performing the analyzing operation in the immunoanalyzer 10, when the user executes the immune analysis application program 71a with the computer 70, the setup screen 72 is displayed on the display unit 52 as shown in FIG. 9. In such setup screen 72, the proceeding state of the analyzing operation in the immunoanalyzer 10 can be monitored, and the user can perform various operations (registration of analysis order, data management, supplement of reagent and consumable goods, etc.) on the immunoanalyzer 10 through a so-called touch panel method of directly touching the setup screen 72 of the display unit 52 with fingers.

As shown in FIG. 9, the setup screen 72 is mainly configured by a an operation button region 73 including menu button group 73a, a measurement interruption button 73b, a measurement start button 73c, a cunsumable part supplement button 73d, a reagent replacement button 73e, and a liquid waste box reset button 73f; and an analyzing operation display region 74 including a consumable part icon part 74a, a waste box icon part 74b, a cunsumable part indicator display part 74c, and a reagent set display unit 74d.

The setup screen 72 is provided with the consumable part icon part 74a which display color changes step-wise according to the remaining quantity of the consumable part based on the detection by the sensor (remaining quantity sensor 21c and remaining quantity sensor 30c etc.), and a consumable part indicator display part 74c. Therefore, the supplement period to each supplying section of the consumable part (reagent, pipette tip 80, and cuvette 90 etc.) can be notified with respect to the user.

Figure 10:
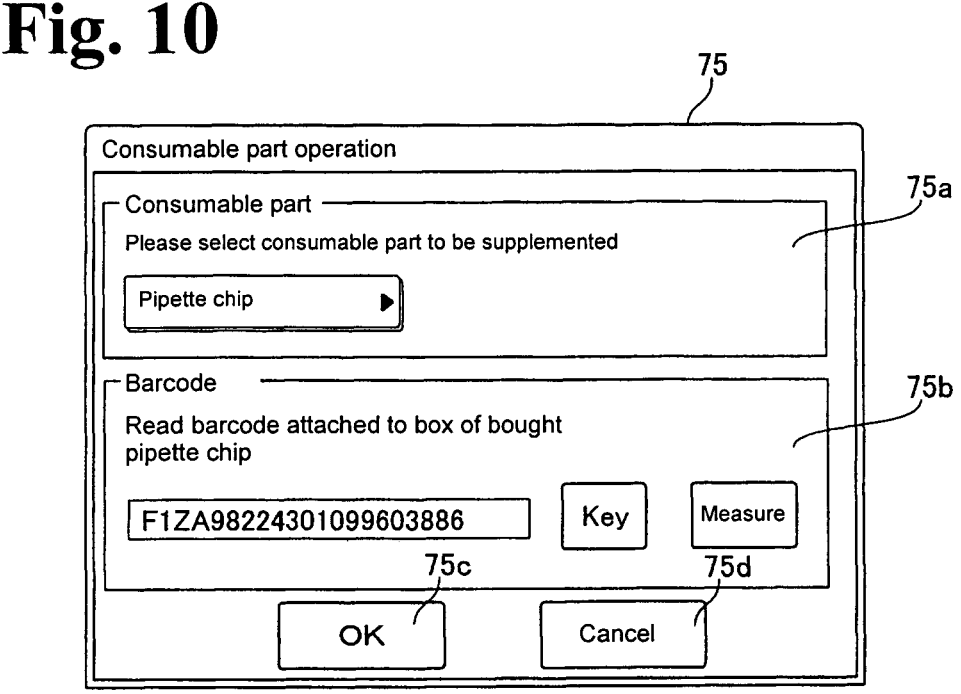
FIG. 10 is a view showing an operation screen displayed when supplementing a consumable part in the operation screen shown in FIG. 9.
Figure 11:
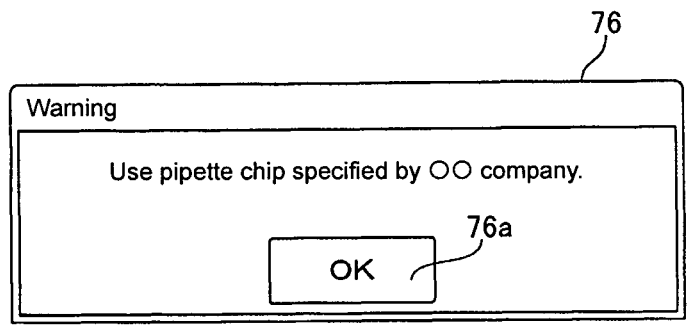
FIG. 11 is a view showing a warning screen displayed when supplementing the consumable part in the operation screen shown in FIG. 9.
Figure 12:
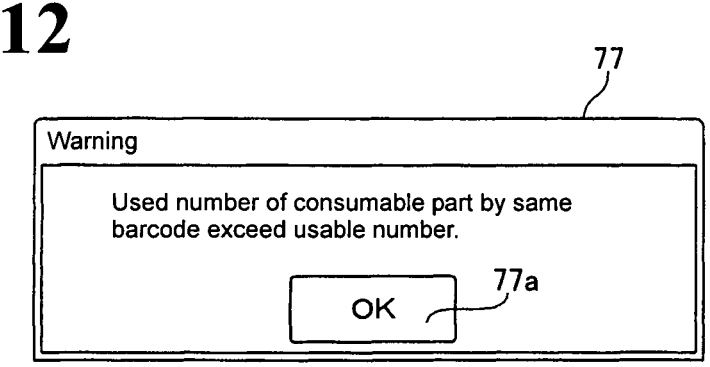
FIG. 12 is a view showing a warning screen displayed when supplementing the consumable part in the operation screen shown in FIG. 9.

In the present embodiment, when the supplement sign of the consumable part is displayed on the consumable part indicator display part 74c, a consumable part operation screen 75 (see FIG. 10) is displayed when the user pushes the consumable part supplement button 73d (see FIG. 9). As shown in FIG. 10, the consumable part operation screen 75 is configured by a consumable part selection part 75a, a barcode information input part 75b, an OK button 75c, and a cancel button 75d. The consumable part selection part 75a has the consumable part to be supplemented (either pipette tip 80 or cuvette 90) selectably configured when touched by the user with finger, etc. The consumable part operation screen 75 is configured such that the OK button 75c is pressed after the barcode information arranged on the side surface of the package (box 81 (see FIG. 8)) of the consumable part is read and input by the barcode reader 60 with respect to the selected consumable part.

Furthermore, in the present embodiment, when the barcode information of the consumable part (assuming pipette tip 80 is selected) read through the barcode reader 60 of the measurement control unit 34 does not match the barcode information managed in the hard disc 51d of the data processing control unit 51, a warning screen 76 (see FIG. 11) is displayed. The warning screen 76 is displayed to notify the user that the manufacturer information of the pipette tip 80 does not match the manufacturer information (registered manufacturer information) registered in the hard disc 51d. Thus the user can recognize whether or not the consumable part (pipette tip 80) to be supplemented is adapted for the immunoanalyzer 10.

Furthermore, in the present embodiment, when the barcode information (serial number) arranged on the package (the box 81 (see FIG. 8)) of the pipette tip 80 to be supplemented for the first time is read, the number of pipette tips 80 (2000) to be newly supplemented is added to the counter 35a of the computer program 35 by referencing the same barcode information (serial number) registered in advance in the hard disc 51d. Therefore, when the user first supplements only the pipette tip 80 (500) contained in one small bag 82, the same barcode information (serial number) can be accepted (permit supplement) for three more times at a later time.

In the present embodiment, when the same barcode information (serial number) is read for more than or equal to a predetermined times (four times), a warning screen 77 (see FIG. 12) is displayed. The user can then recognize that the usable number (2000) of the pipette tip 80 which supplement is permitted by the barcode information is exceeded.

When supplement is completed after the supplement of the pipette tip 80 is appropriately performed, a supplement completed screen 78 (see FIG. 13) is displayed.

In the present embodiment, when the pipette tip 80 stored in the counter 35a runs out in the middle of the analyzing operation, a warning screen 79 (see FIG. 14) is displayed.

The screen configuration for when supplementing the pipette tip 80 is described above, but the user can supplement the cuvette 90 through a similar method through the setup screen 72 when supplementing the cuvette 90.

The used pipette tip 80 and cuvette 90 is accumulated in the waste box (not shown) arranged at the lower part of the measurement mechanism section 20, and the display color of the waste box icon part 74b of the setup screen 72 changes when exceeding a predetermined number. The period of disposing the used consumable part accumulated in the waste box can then be notified to the user.

The operation of supplementing the pipette tip 80 to the immunoanalyzer 10 according to the present embodiment will now be described with reference to FIGS. 1, 4, and 9 to 17.

Figure 15:
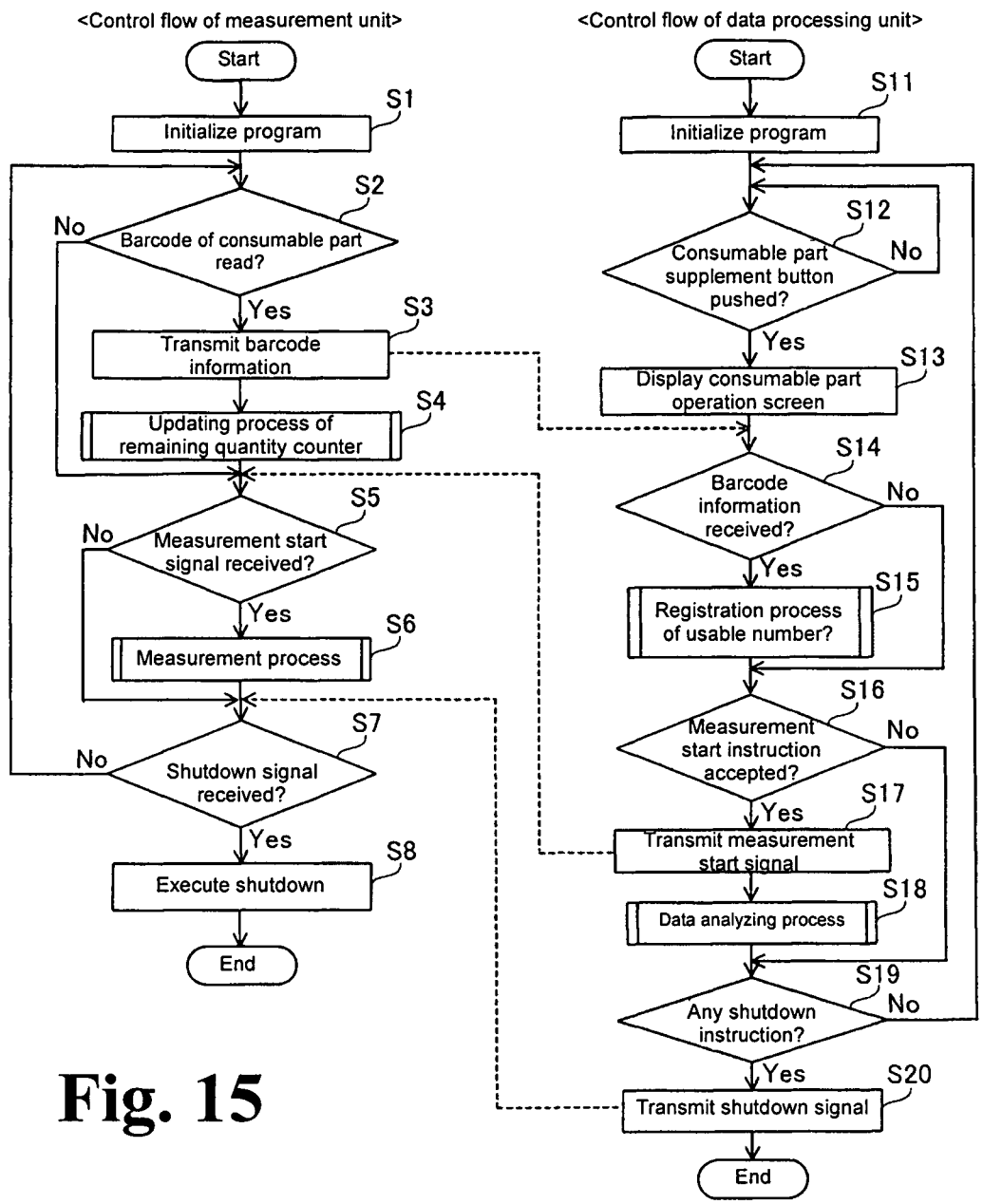
FIG. 15 is a flowchart showing a control operation of an application program in the immunoanalyzer according to one embodiment of the present invention.

First, when the power (not shown) of the measurement mechanism section 20 is turned ON, the measurement control unit 23 is initialized (program is initialized) and operation check of each part of the measurement mechanism section 20 is performed in step S1 (see FIG. 15). When the power (not shown) of the control device 50 is turned ON, the data processing control unit 51 is initialized (program is initialized) in step S11 (see FIG. 15). After the initialization of the measurement control unit 34 is completed, the measurement control unit 34 requests for an initialization complete signal indicating completion of initialization of the data processing control unit 51, and reads the barcode of all the reagents set in the reagent installing units 23 and 24 and the barcode of the reagent rack (not shown) when receiving the initialization complete signal. The read barcode information is transmitted from the measurement control unit 34 to the data processing control unit 51, and stored in the hard disc 51d of the data processing control unit 51.

When the user activates the application program 71a, the setup screen 72 is displayed on the display unit 52, as shown in FIG. 9. As shown in FIG. 15, the measurement control unit 34 executes the control flow of steps S2 to S8, and the data processing control unit 51 executes the control flow of steps S112 to S20 based on the communication with the measurement control unit 34, whereby various operations of the measurement mechanism section 20 are performed.

In step S12, determination is made on whether or not the user has pushed (directly touch a predetermined position of the display unit 52 with finger) the consumable part supplement button 73d of the setup screen 72, where if the consumable part supplement button 73d is not pushed, determination is repeated until the consumable part supplement button 73d is pushed. The user determines whether or not supplement of the pipette tip 80 is necessary by recognizing the display color of the consumable part icon part 74a and the consumable part indicator display part 74c of the setup screen 72, and pushes the consumable part supplement button 73d of the setup screen 72 when determining that supplement is necessary. When the consumable part supplement button 73d is pushed, the consumable part operation screen 75 is displayed in step S13, as shown in FIG. 10.

The user performs reading and input of the barcode 83 of the box 81 containing the pipette tip 80 to be supplemented by means of the barcode reader 60 according to the consumable part operation screen 75.

In step S2, the measurement control unit 34 determines whether or not the barcode 83 arranged on the box 81 containing the pipette tip 80 to be supplemented has been read when the user performs reading and input with the barcode reader 60. If the reading and input of the barcode 83 is not performed, the process proceeds to step S5.

When determined that the barcode 83 has been read in step S2, the barcode information ("manufacturing company information (genuine part manufactured by oo company)", "type (pipette tip)", "lot number", and "serial number") are transmitted to the data processing control unit 51 in step S3. In step S4, the measurement control unit 34 executes "updating process of remaining quantity counter".

In step S14, the data processing control unit 51 determines whether or not the barcode information of the pipette tip 80 from the measurement control unit 34 is obtained (received). When the barcode information of the pipette tip 80 is received, "registration process of usable number" is executed in step S15.

If the barcode information of the pipette tip 80 is not received in step S14, step S15 ("registration process of usable number") is not executed, and the process proceeds to step S16.

In step S16, the data processing control unit 51 determines whether or not the measurement start button 73c has been pushed by the user (whether or not measurement start instruction has been received), and transmits the measurement start signal to the measurement control unit 34 in step S17 when the measurement start button 73c is pushed.

Thus, in step S5, the measurement control unit 34 determines whether or not the measurement start signal transmitted from the data processing control unit 51 in step S17 has been received, and executes "measuring process" in step S6 when the measurement start signal is received.

In step S18, the data processing control unit 51 executes "data analyzing process" of measurement data of the specimen obtained by the measurement section.

In step S19, determination is made on whether or not the user has made a shutdown instruction by the setup screen 72, and the process returns to step S12 if the shutdown instruction has not been made. If determined that the user has made the shutdown instruction in step S19, the shutdown signal is transmitted to the measurement control unit 34 in step S20. The present control is then terminated.

In step S7, the measurement control unit 34 determines whether or not the shutdown signal transmitted from the data processing control unit 51 in step S20 has been received, where the process returns to step S2 and continues the processing operation related to measurement if the shutdown signal has not been received. In step S7, when determined that the shutdown signal transmitted from the data processing control unit 51 has been received, the shutdown signal is executed in step S8. The present control is then terminated.

Figure 16:
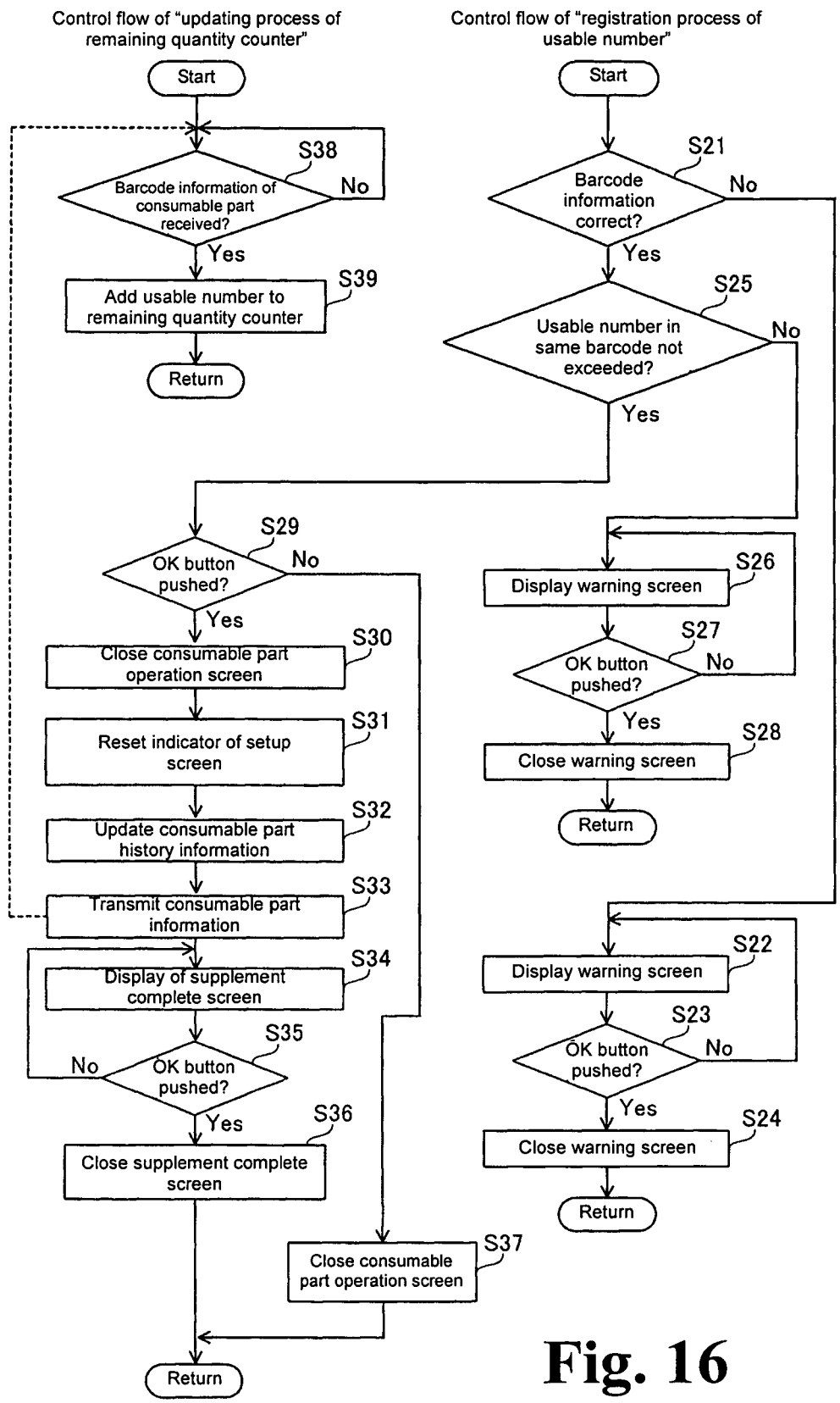
FIG. 16 is a flowchart showing a control operation of the application program in the immunoanalyzer according to one embodiment of the present invention.

The details of the "registration process of usable number" of step S15 by the data processing control unit 5 shown in FIG. 15 will now be described with reference to FIG. 16. In the "registration process of usable number", the data processing control unit 51 executes the control flow shown in FIG. 16. First, in step S21, determination is made on whether or not the read barcode information ("manufacturing company information (genuine part manufactured by oo company)", "type (pipette tip)", "lot number" and "serial number") of the pipette tip 80 are correct.

In the present embodiment, if the read barcode information (manufacturer information) of the pipette tip 80 does not match the manufacturer information (registered manufacturer information) stored in the hard disc 51d in advance, the warning screen 76 is displayed in step S22. In step S23, determination is made on whether or not the user has pushed (directly touch a predetermined position of the display unit 52) the OK button 76a, and if the OK button 76a has not been pushed, the warning screen 76 is continuously displayed and such determination is repeated until the OK button 76a is pushed. If determined that the user has pushed the OK button 76a in step S23, the warning screen 76 is closed in step S24. The present control flow is then terminated.

If determined that the read barcode information (manufacturer information) of the pipette tip 80 match the manufacturer information (registered manufacturer information) stored in the hard disc 51d in advance, the data processing control unit 51 determines whether the usable number (2000) at the same barcode has not been exceeded in step S25. Specifically, since the barcode information is added to the counter 35a (set to the computer program 35 executed by the measurement control unit 34) with 2000 as the usable number in step S33 to be described later when the barcode information of the same pipette tip 80 has already been read in the past, the data processing control unit 51 can accept the same barcode information up to a total of four times (500 in small bag 82×4=2000) including the reading input for the current time.

In the present embodiment, if the usable number (2000) at the same barcode is exceeded, the warning screen 77 is displayed in step S26. In step S27, determination is made on whether or not the user has pushed the OK button 77a (directly touch a predetermined position of the display unit 52 with finger), where if the OK button 77a is not pushed, the warning screen 77 is continuously displayed, and the determination is repeated until the OK button 77a is pushed. If determined that the user has pushed the OK button 77a in step S27, the warning screen 77 is closed in step S28. The present control flow is then terminated.

If determined that the usable number (2000) in the same barcode has not been exceeded in step S25, determination is made on whether or not the user has pushed the OK button 75c of the consumable part operation screen 75 (directly touch a predetermined position of the display unit 52 with finger) in step S29, where if the OK button 75c is not pushed (cancel button 75d is pushed), the consumable part operation screen 75 is closed in step S37. The present control flow is then terminated. In this case, since supplement of the pipette tip 80 is not performed, the consumable part icon part 74a and the consumable part indicator display part 74c of the setup screen 72 continue to display the supplement sign, and the analyzing operation by the measurement mechanism section 20 continue to maintain a stopped state.

If determined that the user has pushed the OK button 75c of the consumable part operation screen 75 in step S29, the consumable part operation screen 75 is closed in step S30. The user then supplements the pipette tip 80 to the containing section 21a of the pipette tip supplying unit 21 from the segmented small bags 82 in the box 81.

In step S31, the color of the consumable part icon part 74a and the consumable part indicator display part 74c of the setup screen 72 is reset (change to color indicating that remaining quantity of pipette tip 80 is in normal range). In step S32, the history information of the supplemented pipette tip 80 is updated and stored in the information stored in the hard disc 51d in advance. In step S33, the data processing control unit 51 transmits the barcode information of the pipette tip 80 updated in step S32 to the measurement control unit 34.

The measurement control unit 34 thus executes the "updating process of remaining quantity counter" of step S4 shown in FIG. 15. In "updating process of remaining quantity counter", the measurement control unit 34 executes the control flow shown in FIG. 16. The details of the "updating process of remaining quantity counter" will be described below with reference to FIG. 16.

In the "updating process of remaining counter", the measurement control unit 34 first determines whether or not the information (barcode information) of the pipette tip 80 transmitted from the data processing control unit 51 in step S33 above is received in step S38, and repeats the determination until the information of the pipette tip 80 is received if the information of the pipette tip 80 is not received.

In the present embodiment, if determined that the information (barcode information) of the pipette tip 80 is received in step S38, the measurement control unit 34 adds the usable number (2000) to the counter 35a set as a variable in the computer program 35 in step S39. The present control is then terminated.

Figure 13:
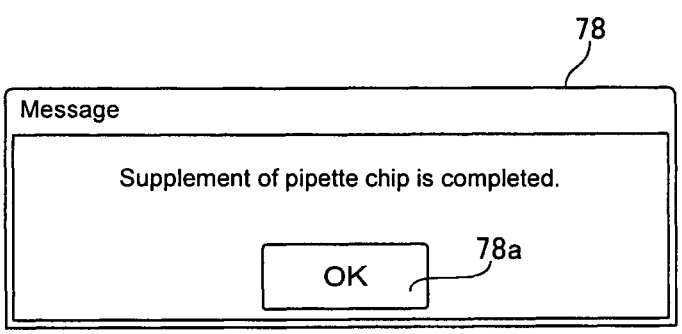
FIG. 13 is a view showing a screen displayed when supplement of the consumable part is completed in the operation screen shown in FIG. 9.

In step S34, the data processing control unit 51 displays the supplement complete screen 78, as shown in FIG. 13. In step S35, determination is made on whether or not the user has pushed the OK button 78a of the supplement complete screen 78, where if the OK button 78a is not pushed, the supplement complete screen 78 is continuously displayed, and the determination is repeated until the OK button 78a is pushed. If determined that the user has pushed the OK button 78a in step S35, the supplement complete screen 78 is closed in step S36. The present control flow is then terminated.

Figure 17:
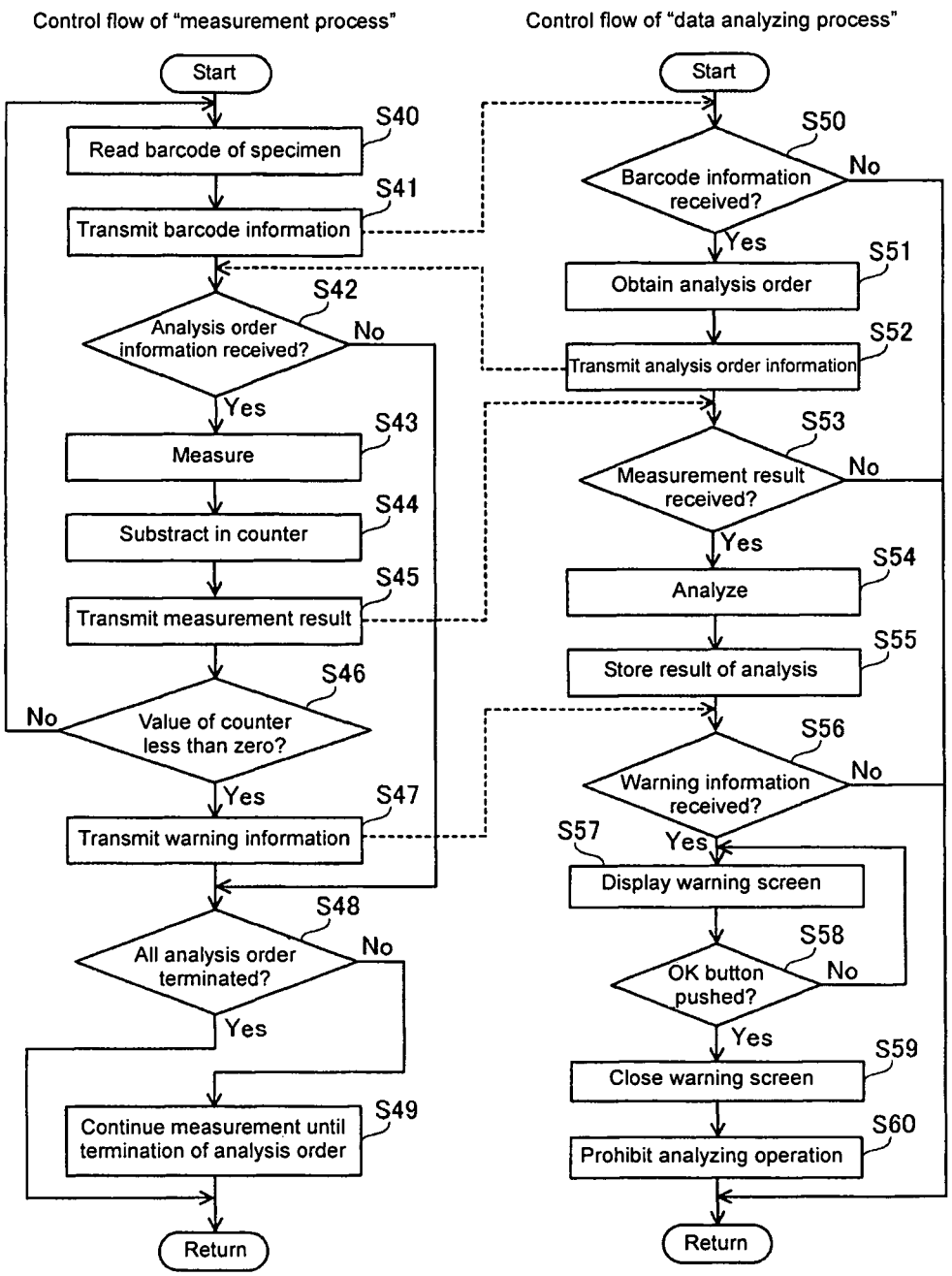
FIG. 17 is a flowchart showing a control operation of the application program in the immunoanalyzer according to one embodiment of the present invention.

The details of the "measuring process" of step S6 by the measurement control unit 34 and the "data analyzing process" of step S18 by the data processing control unit 51 shown in FIG. 15 will now be described with reference to FIG. 17. As shown in FIG. 17, the measurement control unit 34 executes the control flow of steps S40 to S49, and the data processing control unit 51 executes steps S50 to S60 based on communication with the measurement control unit 34, whereby "measuring process" and "data analyzing process" of the specimen are performed.

First, in step S40, the measurement control unit 34 reads the barcode information ("subject name", "collected date and time" etc.) of the test tube 100 injected with the specimen. In step S41, the barcode information of the test tube 100 is transmitted to the data processing control unit 51.

In step S50, the data processing control unit 51 determines whether the barcode information (patient ID etc.) of the test tube 100 injected with the specimen is obtained from the measurement control unit 34, and terminates the present control flow if the barcode information of the test tube 100 is not normally obtained. If determined that the barcode information of the test tube 100 is normally obtained in step S50, the analysis order from the user is obtained in step S51. In step S52, the analysis order information (number of measurements of specimen, etc.) is transmitted to the measurement control unit 34.

In step S42, the measurement control unit 34 determines whether or not the analysis order information (number of measurement of specimen, etc.) transmitted from the data processing control unit 51 in step S52 is received, and performs the measurement in step s43 if the analysis order information is received. In step S44, the measurement control unit 34 detects the rotating operation of the arm 22d of the specimen dispensing arm 22 (see FIG. 1) to subtract the usable number of the pipette tip 80 in the counter 35a (subtract one from 2000 for each one measurement), and transmits the measurement result to the data processing control unit 51 in step S45.

The data processing control unit 51 then determines whether or not the measurement result is received from the measurement control unit 34 in step S53, and terminates the present control flow if the measurement result is not received. If determined that the measurement result (measurement data) from the measurement control unit 34 is normally received in step S53, the measurement result is analyzed in step S54. The result of analysis is stored in the hard disc 51d in step S55.

In step S46, the measurement control unit 34 determines whether or not the value of the counter 35a performed with subtraction in step S44 is less than zero in step S46, and returns the process to step S40 and continues the processing operation related to the measurement of the next specimen if the value of the counter 35a is not less than zero.

In the present embodiment, if determined that the value of the counter 35a is less than zero in step S46, the warning information is transmitted to the data processing control unit 51 in step S47. The data processing control unit 51 then executes the processes after step S56 (steps S57 to S60).

In step S48, the measurement control unit 34 determines whether or not all the analysis orders are terminated in step S48, and terminates the present control if determined that all the analysis orders are terminated.

In the present embodiment, if all the analysis orders are not terminated in step S48, the measurement is continued until all the analysis orders are terminated in step S49. The analyzing operation on the analysis orders that have already been accepted is thereby performed until the end without being interrupted, and then the present control is terminated.

In step S56, the data processing control unit 51 determines whether or not the warning information transmitted from the measurement control unit 34 in step S47 is received in step S56, and terminates the present control flow if the warning information is not received from the measurement control unit 34.

Figure 14:
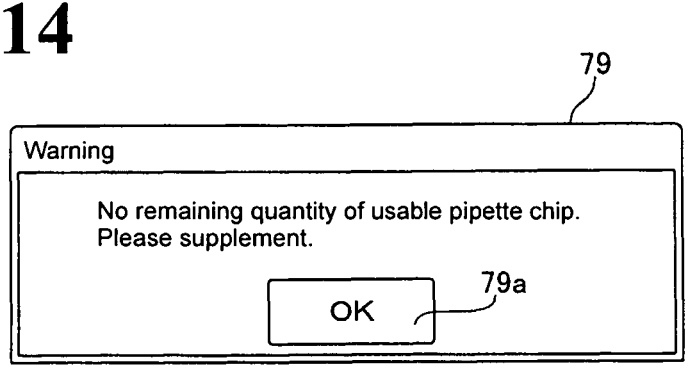
FIG. 14 is a view showing a warning screen displayed when the immunoanalyzer according to one embodiment shown in FIG. 1 performs an analyzing operation.

In the present embodiment, if determined that the warning information from the measurement control unit 34 is received in step S56, the warning screen 79 as shown in FIG. 14 is displayed in step S57. In step S58, determination is made on whether or not the user has pushed the OK button 79a (directly touch a predetermined position of the display unit 52 with finger), where if the OK button 79a is not pushed, the warning screen 79 is continuously displayed, and the determination is repeated until the OK button 79a is pushed. If determined that the user has pushed the OK button 79a in step S58, the data processing control unit 51 closes the warning screen 79 in step S59. In step S60, the data processing control unit 51 prohibits the analyzing operation by not accepting the push of the measurement start button 73c by the user. The present control flow is then terminated.

In the present embodiment, the pipette tip 80 is supplemented to the immunoanalyzer 10 and the analyzing operation of the specimen is performed in the above manner. The processing operation similar to the supplement method of the pipette tip 80 is performed by the application program 71a when the user supplements the cuvette 90 to the cuvette supplying unit 30.

In the present embodiment, the user can be warned when the actually used number of pipette tips 80 becomes greater than the usable number (2000) of the pipette tip 80 obtained by the barcode reader 60 in advance by providing warning screens 76, 77, and 79 for giving a predetermined warning to the user, and the measurement control unit 34 and the data processing control unit 51 for giving a warning through the warning screens 76, 77, and 79 when the relationship between usable number reflecting the number of pipette tips 80 managed by the barcode 83 attached to the box 81 and the used number of pipette tips 80 supplemented from the box 81 is a predetermined relationship as described above. Thus, the analyzing operation is performed with the adaptability of the pipette tip 80 to be used to the sample analyzer 1 managed. The lowering in measurement precision that occurs when the pipette tip 80 that is not adaptable is used can be suppressed. The measurement precision in the analyzing operation thus can be maintained at a predetermined level by using the pipette tip 80 adapted for the immunoanalyzer 10.

In the present embodiment, the measurement control unit 34 and the data processing control unit 51 are configured to give a warning through the warning screen 79 when the number of used pipette tips 80 supplemented from the box 81 exceeds usable number (2000). Thus, the user can easily recognize that the there is no remaining quantity (remaining number) of usable pipette tip 80 registered in advance by recognizing the warning through the warning screen 79.

In the present embodiment, the measurement control unit 34 and the data processing control unit 51 determines the presence or absence of analysis order when the used number of pipette tips 80 supplemented from the box 81 exceeds the usable number (2000); where if the analysis order is being requested, the analyzing operation of the specimen is prohibited by not accepting the push of the measurement start button 73c by the user after completing the analyzing operation based on the analysis order. The analyzing operation on the already accepted analysis order is thus suppressed from being interrupted even if the remaining quantity (remaining number) of usable pipette tips 80 becomes zero. If the push of the measurement start button 73c is not accepted with respect to the new analysis order, the user cannot execute the analyzing operation on the new analysis order unless the user re-supplies the pipette tip 80 adapted for the immunoanalyzer 10. Therefore, lowering in analyzing precision that occurs when the non-adapted pipette tip 80 is used for the new analysis order is suppressed, whereby the analyzing precision can be maintained at a predetermined level.

In the present embodiment, the measurement control unit 34 and the data processing control unit 51 further control the operation of the pipette tip supplying unit 21, and determines the presence or absence of the analysis order when the used number of pipette tips 80 supplemented from the box 81 exceeds the usable number (2000), and prohibits the operation of the pipette tip supplying unit 21 after completing the analyzing operation based on the analysis order when the analysis order is being requested. Thus, the analyzing operation of the specimen on the new analysis order can be easily prohibited while suppressing the analyzing operation on the already accepted analysis order from being interrupted.

In the present embodiment, the measurement control unit 34 and the data processing control unit 51 determines the presence or absence of the analysis order when the user number of pipette tips 80 supplemented from the box 81 exceeds the usable number (2000), and prohibits the analyzing operation of a sample when the analysis order is not being requested. Thus, after the used number of pipette tips 80 exceeds the usable number, the analyzing operation can be easily prohibited from being performed on the new analysis order.

In the present embodiment, the measurement control unit 34 and the data processing control unit 51 include the RAM 43c for storing the serial number obtained by the barcode reader 60, and give a warning through the warning screen 79 when the serial number obtained by the barcode reader 60 and the serial number already stored in the RAM 34c match, and the used number of pipette tips 80 belonging to a group stored in the RAM 34c (managed as one group by the same barcode information) exceeds the usable number (2000). When newly supplementing the pipette tip 80, the user then can recognize that the actually used number of pipette tip 80 has reached the usable number of pipette tip 80 registered as the usable number of the same serial number in advance. The user can thus easily recognize that the pipette tip 80 having a different serial number needs to be supplemented.

In the present embodiment, the barcode 83 holds the serial number and the manufacturer information indicating as being the pipette tip 80 adapted for the immunoanalyzer 10, and the hard disc 51d stores the registered manufacturer information corresponding to the manufacturer information in advance and also can store the serial number. The measurement control unit 34 and the data processing control unit 51 are configured to store the serial number and the type of pipette tip 80 corresponding to the relevant group in the hard disc 51d when the manufacturer information obtained by the barcode 83 and the registered manufacturer information match, and when the serial number is not stored in the hard disc 51d. The measurement control unit 34 and the data processing control unit 51 then can easily check the registered manufacturer information stored in advance in the hard disc 51d and the manufacturer information read from the barcode 83, and easily manage the serial number of the pipette tip 80 and the type of consumable part with the hard disc 51d.

In the present embodiment, the measurement control unit 34 and the data processing control unit 51 are configured to give the warning through the warning screen 76 when the manufacturer information obtained by the barcode 83 and the registered manufacturer information do not match. By the warning given through the warning screen 76, the user can easily recognize that the pipette tip 80 to be newly supplied is not the pipette tip 80 adapted for the immunoanalyzer 10.

In the present embodiment, the measurement control unit 34 and the data processing control unit 51 are configured to five a warning through the warning screen 77 when the manufacturer information obtained by the barcode 83 and the registered manufacturer information match, and when the reading number of times of the same barcode information exceeds a predetermined number of times (four times). When the user supplements the pipette tip 80 having the same serial number over plural times, the user can easily recognize that the pipette tip 80 having the same serial number cannot be supplemented by greater than or equal to the usable number (2000) stored in advance as the total number by the warning given through the warning screen 77.

When supplementing the cuvette 90 serving as a consumable part to the cuvette supplying unit 30 of the immunoanalyzer 10 as well, effects similar to the above effects are obtained according to the configuration described in the present embodiment.

The embodiment disclosed herein is illustrative in all aspects and should not be construed as being exclusive. The scope of the present invention is defined by the attached claims rather than by the description of the embodiments, and meaning equivalent to the claims and all changes within the scope of the claims are all enclosed therein.

For instance, an example of applying the present invention to the immunoanalyzer 10 has been described in the above embodiment, but the present invention is not limited thereto, and may be applied to other analyzers such as biochemical analyzer and blood coagulation measurement device.

In the present embodiment, the measurement control unit 34 and the data processing control unit 51 are configured to determine the presence or absence of analysis order when the user number of pipette tip 80 exceeds the usable number (2000) stored in the counter 35a, and to prohibit the operation of the pipette tip supplying unit 21 after completing the analyzing operation based on the analysis order if the analysis order is being requested, but the present invention is not limited thereto. The measurement control unit 34 and the data processing control unit 51 may be configured to store the user number of pipette tip 80 to the counter 35a, and accept the analysis order even if the value obtained by subtracting the used number of pipette tip 80 from the usable number (2000) stored in the counter 35a is less than the number of analysis order. According to such variant, the analysis order can be accepted and the analyzing operation can be performed even if the remaining quantity (remaining number) of usable pipette tip 80 becomes less than the number of analysis order.

In the above embodiment, the measurement control unit 34 is configured to recognize the usable number of consumable parts by referencing the serial number registered in the hard disc 51d in advance with respect to the barcode information (serial number) obtained from the barcode 83, but the present invention is not limited thereto. Since the barcode information obtained from the barcode 83 includes information related to the usable number of consumable part, the measurement control unit 34 may be configured to directly recognize the re-supplying number of consumable part. According to such variant as well, in the analyzing operation, the measurement control unit 34 and the data processing control unit 51 can warn the user when the used number becomes greater than the re-supplying number of consumable part by recognizing the actually used number of consumable part with respect to the usable number (re-supplying number) of consumable part obtained by the barcode reader 60 in advance. Thus, the analyzing operation can be performed with the adaptability of the consumable analyzer to be re-supplied to the sample analyzer managed. The lowering in measurement precision that occurs when the non-adapted consumable part is used can be suppressed. The measurement precision in the analyzing operation can be maintained at a predetermined level by using the consumable part adapted for the immunoanalyzer 10.

In the embodiment, the barcode 83 is arranged on the side surface of the box 81 containing four small bags 82, but the present invention is not limited thereto, and the barcode 83 may be arranged for every small bag 82, and the barcode information (serial number etc.) can be obtained from the barcode 83 of the small bag 82 with the barcode reader 60. According to such variant, the information management of the consumable part can be easily performed with the segmented small bag 82 as a unit.

In the embodiment, a warning is given to the user by displaying the warning screen on the display unit, but the present invention is not limited thereto, and a warning may be given to the user through voice.

In the embodiment, the operation screen such as the setup screen 72 is operated through a touch panel method of the display unit 52, but the present invention is not limited thereto, and may be operated through a mouse or a keyboard connected to the personal computer.

What is claimed is:

1. A sample analyzer for analyzing a sample using a consumable part, comprising:
   a measurement mechanism section configured to obtain measurement data associated with the sample and associated with an analysis order received from user;
   an identification information obtainer for obtaining group identification information for identifying a group of a plurality of consumable parts comprising at least one of a plurality of pipette tips or a plurality of cuvettes;
   a consumable part holder for holding the consumable parts used by the measurement mechanism section; and
   a computer processor and a memory comprising a computer program that enables the processor to:
      obtain a number of the consumable parts which have been used by the measurement mechanism section;

obtain a number of the consumable parts included in the group, based on the group identification information obtained by the identification information obtainer;

determine whether the number of consumable parts which have been used by the measurement mechanism section exceeds the number of consumable parts included in the group; and based on a determination that the number of consumable parts which have been used by the measurement mechanism section exceeds the number of consumable parts included in the group:

provide the user with a warning;

determine whether the measurement mechanism section has completed the analysis order received from the user; and based on a determination that the analysis order is not complete, cause the measurement mechanism section to continue measurement associated with the analysis order until the analysis order is complete.

2. The sample analyzer of claim 1, wherein the computer processor is further programmed to:

determine presence or absence of an analysis order when the number of consumable parts which have been used by the measurement mechanism section exceeds the number of consumable parts included in the group; and prohibit an analyzing operation of a sample after an analyzing operation based on the analysis order is completed, when the analysis order is present.

3. The sample analyzer of claim 2, wherein the computer processor is further programmed to prohibit an analyzing operation of a sample when the analysis order is not present.

4. The sample analyzer of claim 2, further comprising:

a consumable part supplier for supplying the consumable parts held by the consumable holder to the measurement mechanism section; and wherein the computer processor is further programmed to control the consumable part supplier so as to stop supplying a consumable part to the measurement mechanism section after the analyzing operation based on the analysis order is completed, when the analysis order is present.

5. The sample analyzer of claim 1, wherein the group identification information includes first collation information indicating that the consumable parts are adapted for the sample analyzer, the memory stores second collation information corresponding to the first collation information, the computer processor is programmed to provide the warning when the first collation information obtained by the identification information obtainer does not correspond to the second collation information stored in the memory.

6. The sample analyzer of claim 5, wherein the memory is further configured to store the group identification information obtained by the identification information obtainer; and the computer processor is further programmed to store, in the memory, the group identification information and a type of the consumable parts corresponding to the group, when the first collation information obtained by the identification information obtainer corresponds to the second collation information stored in the memory and when the group identification information is not stored in the memory.

7. The sample analyzer of claim 5, wherein the first and second collation information include manufacturer information indicating a manufacturer of the consumable part.

8. The sample analyzer of claim 1, further comprising a consumable part supplier for supplying the consumable parts held by the consumable holder to the measurement mechanism section, wherein the computer processor is programmed to obtain the number of the consumable parts which have been used by the measurement mechanism section based on a number of times the consumable part supplier supplies the consumable part to the measurement mechanism section.

9. The sample analyzer of claim 1, further comprising a consumable part supplier for supplying the consumable parts held by the consumable holder to the measurement mechanism section, wherein the consumable part is a pipette tip;

the measurement mechanism section comprises a dispenser for dispensing the sample; and the computer processor is programmed to obtain the number of pipette tips which have been used by the measurement mechanism section based on a number of times the consumable part supplier supplies the pipette tip to the dispenser.

* * * * *

UNITED STATES PATENT AND TRADEMARK OFFICE
CERTIFICATE OF CORRECTION

PATENT NO.            : 8,535,607 B2                                  Page 1 of 1
APPLICATION NO.       : 12/079797
DATED                 : September 17, 2013
INVENTOR(S)           : Yuji Wakamiya et al.

It is certified that error appears in the above-identified patent and that said Letters Patent is hereby corrected as shown below:

In the Claims

In column 18, claim 1, line 57, after "order receive from" insert --a--.

Signed and Sealed this
Twenty-fifth Day of March, 2014

Michelle K. Lee
*Deputy Director of the United States Patent and Trademark Office*